United States Patent [19]

Lagrange et al.

[11] Patent Number: 5,792,221
[45] Date of Patent: Aug. 11, 1998

[54] HYDROXYPROPYLATED 2-NITRO-P-PHENYLENEDIAMINES, AND COMPOSITIONS FOR DYEING KERATINOUS FIBERS WHICH CONTAIN HYDROXYPROPYLATED 2-NITRO-P-PHENYLENEDIAMINES

[75] Inventors: Alain Lagrange, Coupvray; Alex Junino, Livry-Gargan; Alain Genet, Aulnay-sous-Bois; Jean Cotteret, Verneuil-sur-Seine, all of France

[73] Assignee: L'Oreal, Paris, France

[21] Appl. No.: 755,628

[22] Filed: Nov. 25, 1996

Related U.S. Application Data

[63] Continuation of Ser. No. 351,241, Dec. 7, 1994, abandoned.

[30] Foreign Application Priority Data

Jun. 19, 1992 [FR] France .................... 92/07515

[51] Int. Cl.$^6$ .................... A61K 7/13; C07C 211/29
[52] U.S. Cl. .................... 8/415; 8/405; 8/407; 8/414; 8/426; 8/649; 564/441
[58] Field of Search .................... 8/405, 415, 649, 8/414, 407, 426; 564/306, 400, 441

[56] References Cited

U.S. PATENT DOCUMENTS

| | | | |
|---|---|---|---|
| 2,750,326 | 6/1956 | Eckardt et al. | 8/415 |
| 2,750,327 | 6/1956 | Eckardt et al. | 8/415 |
| 3,168,442 | 2/1965 | Brunner et al. | 8/415 |
| 3,274,249 | 9/1966 | Brunner et al. | 8/415 |
| 3,446,567 | 5/1969 | Augustin et al. | 8/415 |
| 3,488,138 | 1/1970 | Iscowitz | 8/415 |
| 3,555,584 | 1/1971 | Kalopissis et al. | 8/415 |
| 3,951,589 | 4/1976 | Alperin et al. | 8/415 |
| 4,007,228 | 2/1977 | Kalopissis et al. | 260/573 |
| 4,601,726 | 7/1986 | Grollier et al. | 8/415 |
| 4,725,283 | 2/1988 | Cotteret et al. | 8/415 |
| 4,981,486 | 1/1991 | Grollier et al. | 8/415 |
| 5,041,143 | 8/1991 | Lang et al. | 8/415 |

FOREIGN PATENT DOCUMENTS

| | | |
|---|---|---|
| 1174816 | 12/1969 | United Kingdom . |
| 2150148 | 6/1985 | United Kingdom . |

*Primary Examiner*—Paul Lieberman
*Assistant Examiner*—Caroline L. Dusheck
*Attorney, Agent, or Firm*—Jacobson, Price, Holman & Stern, PLLC

[57] ABSTRACT

A hydroxypropylated 2-nitro-p-phenylenediamine of formula (I), wherein R1 is a C1–4 alkyl, β-hydroxyethyl, β-hydroxypropyl or γ-hydroxypropyl radical; R2 and R3 independently represent a β-hydroxyethyl, β-hydroxypropyl, γ-hydroxypropyl or β,γ-dihydroxypropyl radical, with the proviso that at least one of R1, R2 and R3 is a γ-hydroxypropyl radical, while the other two are not both a β-hydroxyethyl radical; and cosmetically acceptable salts thereof. This compound may be used for directly dyeing hair to give blue through purplish blue shades which are wash-fast, light-fast, waterproof and sweat resistant.

17 Claims, No Drawings

HYDROXYPROPYLATED 2-NITRO-P-PHENYLENEDIAMINES, AND COMPOSITIONS FOR DYEING KERATINOUS FIBERS WHICH CONTAIN HYDROXYPROPYLATED 2-NITRO-P-PHENYLENEDIAMINES

This is a continuation of application Ser. No. 08/351,241, filed Dec. 7, 1994, now abandoned.

The present invention relates to novel nitrobenzene dyes of hydroxypropylated 2-nitro-p-phenylenediamine type, which are intended for dyeing keratinous fibers and in particular human hair.

In the field of hair dyeing, the use of direct dyes is very widespread since they have certain advantages relative to oxidation dye precursors and, in particular, a reduction in the potential risks of allergy and the absence of a sensitization of the hair caused by the oxidative process.

Nitrobenzene derivatives feature among the most commonly used direct dyes, which derivatives, on the one hand, have a high affinity for hair, and which, on the other hand, due to the variety of possible substituents, make it possible to cover a wide spectrum of shades ranging from yellow to blue and including red.

Among the blue to violet-blue nitrobenzene dyes used, there may in particular be mentioned 1-(β-hydroxyethyl) amino-N,N-bis(β-hydroxyethyl)amino-2-nitrobenzene disclosed in French Patent 1,101,904, 1-(γ-hydroxypropyl) amino-4-N,N-bis(β-hydroxyethyl)amino-2-nitrobenzene disclosed in French Patent 2,570,375, 1-(β-hydroxyethyl) amino-4-(N-methyl-N-β-hydroxyethyl)amino-2-nitrobenzene disclosed in Canadian Patent 900,490, 1-(β-hydroxyethyl)amino-4-(N-ethyl-N-β-hydroxyethyl)amino-2-nitrobenzene disclosed in Patent EP-0,184,061, 1-(β-γ-dihydroxypropyl)amino-4-(N-ethyl-N-β-hydroxyethyl) amino- 2-nitrobenzene disclosed in German Patent 3,616,720 and 1-(β-hydroxyethyl)amino-4-(N-β-hydroxyethyl-N-γ-hydroxypropyl)amino-2-nitrobenzene disclosed in Patent Application GB-A-2,164,959.

However, the formulation of these dyes poses problems on account of their resistance to washing, which is not satisfactory.

The Applicant has thus sought other blue to violet-blue nitrobenzene dyes which have good solubility in water, in water/alcohol mixtures and more generally in the usual dye supports, and which lead, on hair, to dyes which are washfast and also light-fast, weatherproof and sweat-resistant.

As a result of this research, the Applicant has discovered novel 2-nitro-p-phenylenediamines having the formula:

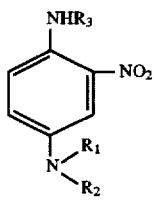
(I)

in which

R₁ represents a $C_1$–$C_4$ alkyl, β-hydroxyethyl, β-hydroxypropyl or γ-hydroxypropyl radical;

R₂ and R₃, independently of one another, represent a β-hydroxyethyl, β-hydroxypropyl, γ-hydroxypropyl or β,γ-dihydroxypropyl radical, at least one of the radicals R₁, R₂ or R₃ representing a γ-hydroxypropyl radical and it not being possible for the other two radicals simultaneously to denote a β-hydroxyethyl radical.

The compounds of formula (I) may be used in free base form or in the form of a base salified with acids such as hydrochloric acid, hydrobromic acid, sulfuric acid, etc. They may thus be found in the form of a hydrochloride, a hydrobromide, a sulfate, etc.

The present invention thus relates to the novel compounds of formula (I) and to the cosmetically acceptable salts thereof.

In the formula (I), the $C_1$–$C_4$ alkyl radical represented by R₁ is a methyl, ethyl, n-propyl, isopropyl, n-butyl, isobutyl or tert-butyl radical.

The preferred compounds of formula (I) are those in which R₁ denotes a methyl, ethyl or n-propyl radical, R₂ denotes a β-hydroxyethyl or γ-hydroxypropyl radical and R₃ denotes a β-hydroxyethyl, β-hydroxypropyl or γ-hydroxypropyl radical.

The preferred compounds (I) are in particular chosen from the following compounds: 1-(γ-hydroxypropyl) -amino-4-(N-ethyl-N-β-hydroxyethyl)amino-2-nitrobenzene, 1-(γ-hydroxypropyl)amino-4-(N-methyl-N-β-hydroxyethyl) -amino-2-nitrobenzene, 1-(γ-hydroxypropyl)amino-4-(N-n -propyl-N-β-hydroxyethyl)amino-2-nitrobenzene, 1-(γ-hydroxypropyl)amino-4-N,N-bis γ-hydroxypropyl) amino-2-nitrobenzene, 1-(β-hydroxyethyl)amino-4,N,N-bis (γ-hydroxypropyl)amino-2-nitrobenzene [sic], 1-(γ-hydroxypropyl)amino-4-(N-β-hydroxyethyl-N-γ-hydroxypropyl)amino -2-nitrobenzene, 1-(γ-hydroxypropyl) amino-4-(N-ethyl-N-γ-hydroxypropyl)amino-2-nitrobenzene, 1-(β-hydroxyethyl -amino-4-(N-ethyl-N-γ-hydroxypropyl)amino-2-nitrobenzene [sic] and 1-(β-hydroxypropyl)amino-4-(N-methyl-N-γ-hydroxypropyl) amino-2-nitrobenzene and the cosmetically acceptable salts thereof.

The present invention also relates to the process for the preparation of the compounds of formula (I).

According to a first embodiment of the process for the preparation of the compounds (I), a 1,4-bis-(hydroxyalkylamino)-2-nitrobenzene of formula:

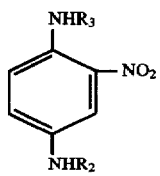
(II)

in which R₂ and R₃ are identical or different and denote a β-hydroxyethyl, β-hydroxypropyl, γ-hydroxypropyl or β-γ-dihydroxypropyl radical, is reacted in aqueous medium with a $C_1$–$C_4$ haloalkane or a $C_1$–$C_3$ haloalkanol of formula R₁X in which R₁ is a $C_1$–$C_4$ alkyl, β-hydroxyethyl, β-hydroxypropyl or γ-hydroxypropyl radical and X is a halogen chosen from chlorine, bromine and iodine, in the presence of calcium carbonate, at a temperature between room temperature and the reflux temperature of the reaction medium, the compound of formula (I) obtained is then collected and, optionally, is purified.

According to another embodiment, the compound of formula (I) in which R₁ and R₂ are identical and represent a β-hydroxyethyl, β-hydroxypropyl or γ-hydroxypropyl radical is prepared by reacting, in a first stage, in aqueous medium, in a boiling water bath, 4-fluoro-3-nitroaniline with a haloalkanol of formula R₂X where R₂ has the meaning indicated above and X is a halogen chosen from chlorine, iodine and bromine, in the presence of calcium carbonate, and, in a second stage, the 4-fluoro -3-nitro-1-N,N-bis (hydroxyalkyl)aminobenzene obtained is reacted in solvent medium, in a boiling water bath, with an alkanolamine of formula R₃NH₂ where R₃ has the meaning indicated above, in order to obtain the compound of formula (I), which is optionally purified.

The present invention also relates to the novel compound obtained in the first stage of the above process consisting of 4-fluoro-3-nitro-1-N,N-bis(γ-hydroxypropyl) aminobenzene.

The compound of formula (II) above can be obtained by reacting a 4-fluoro-3-nitro-1-hydroxyalkyl -aminobenzene of formula:

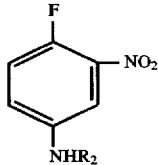

(III)

in which R₂ has the meaning indicated above for the formula (I), with an alkanolamine of formula R₃NH₂ in which R₃ has the meaning indicated above for the formula (I), in solvent medium, in a boiling water bath, in order to obtain the compound of formula:

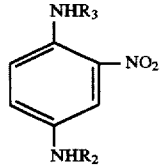

(II)

The present invention also relates to the novel compounds of formula:

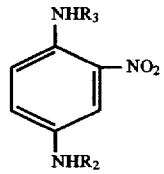

(II')

in which R₂ denotes γ-hydroxypropyl and R₃ denotes β-hydroxyethyl, β-hydroxypropyl or γ-hydroxypropyl, and to the cosmetically acceptable salts thereof.

The compounds of formula (II') above are violet to red dyes which can be used as direct dyes for dyeing keratinous fibers and in particular human hair.

The invention thus also relates to a dye composition for the direct dyeing of keratinous fibers and in particular human hair, which composition contains, in an aqueous, alcoholic or aqueous-alcoholic vehicle, at least one compound of formula (I) indicated above or else at least one compound of formula (II') indicated above or one of the cosmetically acceptable salts thereof.

The Applicant has observed that the use of the blue to violet-blue dye of formula (I) or of the violet to red dye of formula (II'), in combination with one or more yellow or green-yellow dyes, produces, in particular on natural grey hair containing 90% white hairs or on permanent-waved grey hair, natural shades which are more wash-fast, light-fast, weatherproof and sweat-resistant than when the dyes of the prior art are used.

According to a preferred embodiment, the dye composition according to the invention contains a compound of formula (I) or a compound of formula (II'), or one of the cosmetically acceptable salts thereof, in combination with one or more yellow or green-yellow nitrobenzene dyes, which gives, on grey hair containing 90% white hairs, a shade or "hue" of between 2.5 Y and 2.5 GY on the Munsell circle (see Official Digest publication, April 1975, page 375, FIG. 2).

According to a more particularly preferred embodiment of the present invention, the compound of formula (I) or of formula (II') is combined with yellow or green-yellow dyes chosen from the following compounds:

1-β-hydroxyethyloxy-3-methylamino-4-nitrobenzene,
1-(methylamino)-2-nitro-5-(β,γ-dihydroxypropyl) oxybenzene,
1-(β-hydroxyethylamino)-2-methoxy-4-nitrobenzene,
1-(β-aminoethylamino)-2-nitro-5-methoxybenzene,
1,3-di(β-hydroxyethylamino)-4-nitro-6-chlorobenzene,
1-amino-2-nitro-6-methylbenzene,
1-(β-hydroxyethylamino)-2-hydroxy-4-nitrobenzene,
N- (β-hydroxyethyl)-2-nitro-4-trifluoromethylaniline,
4-β-hydroxyethylamino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-β-ureidoethylamino-4-nitrobenzene,
O,N-bis(β-hydroxyethyl)-2-amino-5-nitrophenol,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene,
4-(β-hydroxyethylamino)-3-nitrobenzamide.

According to the invention, the concentration of compound of formula (I) or (II') is between 0.01 and 10% by weight, and preferably between 0.1 and 5% by weight, expressed as free base, relative to the total weight of the composition.

The total concentration of yellow or green-yellow dyes is between 0.05 and 3% by weight, based on the total weight of the composition.

It is, of course, possible to add other nitrobenzene dyes to the combinations of dyes (I) or (II') or of yellow or green-yellow dyes according to the invention, for example red dyes chosen from the following compounds:

1-hydroxy-3-nitro-4-(γ-hydroxypropylamino)benzene,
N-(β-hydroxyethyl)amino-3-nitro-4-aminobenzene [sic],
1-amino-3-methyl-4-(β-hydroxyethyl)amino-6-nitrobenzene,
1-hydroxy-3-nitro-4-N-β-hydroxyethylaminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethylamino)-5-chlorobenzene,
2-nitro-4-aminodiphenylamine,
1-amino-3-nitro-6-hydroxybenzene.

It is also possible to add orange nitrobenzene dyes chosen from the following compounds:

1-(β-aminoethyl)amino-2-nitro-4-(β-hydroxyethyl) oxybenzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethylamino)benzene,
2-nitro-4'-hydroxydiphenylamine,
1-amino-2-nitro-4-hydroxy-5-methylbenzene.

It is also possible to add other direct dyes such as azo dyes, anthraquinone dyes, dyes derived from triarylmethane or basic dyes, among which there may more particularly be mentioned the dyes known under the names "Basic Brown 16", "Basic Yellow 57", "Basic Red 76" and "Basic Blue 99" in the COLOR INDEX, 3rd edition.

The proportion of these red or orange nitrobenzene addition dyes or other direct dyes can vary between 0.05 and 10% by weight of the composition.

The dye composition according to the invention may comprise, as suitable vehicle, water and/or organic solvents which are acceptable from a cosmetic viewpoint, and more particularly alcohols such as ethyl alcohol, isopropyl alcohol, benzyl alcohol and phenylethyl alcohol, or glycols or glycol ethers such as, for example, ethylene glycol and the monomethyl, monoethyl and monobutyl ethers thereof, propylene glycol, butylene glycol and dipropylene glycol, as well as diethylene glycol alkyl ethers such as, for example, diethylene glycol monoethyl ether or monobutyl ether, in concentrations of between 0.5 and 20%, and preferably of between 2 and 10%, relative to the total weight of the composition.

Fatty amides such as the mono- and diethanolamides of acids derived from coconut, from lauric acid or from oleic acid, may also be added to the composition according to the invention, in concentrations of between 0.05 and 10% by weight.

Anionic, cationic, nonionic or amphoteric surface-active agents, or mixtures thereof, may also be added to the composition according to the invention. The surfactants are preferably present in the composition according to the invention in a proportion of between 0.1 and 50% by weight, and advantageously of between 1 and 20% by weight, relative to the total weight of the composition.

Among the surface-active agents, there may more particularly be mentioned anionic surface-active agents which are used alone or as a mixture, in particular such as alkali metal salts, magnesium salts, ammonium salts, amine salts or alkanolamine salts of the following compounds:

alkyl sulfates, alkyl ether sulfates, alkyl amide sulfates which may or may not be ethoxylated, alkyl sulfonates, alkyl amide sulfonates, α-olefin sulfonates;

alkyl sulfoacetates, alkyl phosphates;

fatty acids such as lauric acid, myristic acid, oleic acid, ricinoleic acid, palmitic acid, stearic acid, acids of coconut oil or of hydrogenated coconut oil, carboxylic acids of polyglycol ethers, the alkyl radicals of these compounds having a linear chain of 12 to 18 carbon atoms.

As cationic surface-active agents, there may more particularly be mentioned fatty amine salts, quaternary ammonium salts such as the alkyldimethylbenzylammonium, alkyltrimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long-chain groups which preferably have between 12 and 18 carbon atoms.

Amine oxides may also be mentioned among these compounds of cationic nature.

Among the amphoteric surface-active agents which may be used, there may in particular be mentioned alkylamino (mono- and di)propionates, betaïnes such as alkyl beta ines, N-alkyl sulfobetaïnes, N-alkylamino betaïnes, the alkyl radical having between 8 and 22 carbon atoms, and cycloimidiniums such as alkylimidazolines.

Among the nonionic surfactants which may optionally be used in the compositions in accordance with the invention, there may be mentioned alcohols, α-diols, alkylphenols and amides, which are polyglyclerolated, these compounds containing a $C_8$–$C_{18}$ fatty chain;

alcohols, alkylphenols and fatty acids, which are polyethoxylated, these compounds containing a $C_8$ to $C_{18}$ fatty chain;

condensates of ethylene oxide and of propylene oxide on fatty alcohols; polyethoxylated fatty amides, containing at least 5 mol of ethylene oxide;

polyethoxylated fatty amines.

The thickening products which may be added to the composition according to the invention may advantageously be taken from the group formed by sodium alginate, gum arabic, guar gum, carob gum, xanthan gum, cellulose derivatives such as methylcellulose, hydroxyethylcellulose, hydroxypropylmethylcellulose, the sodium salt of carboxymethylcellulose and acrylic acid polymers.

Inorganic thickening agents such as bentonite may also be used. These thickening agents are used alone or as a mixture, and are preferably present in a proportion of between 0.2 and 5% by weight relative to the total weight of the composition, and advantageously of between 0.5 and 3% by weight.

The dye composition according to the invention may be formulated at acidic, neutral or alkaline pH, the pH possibly ranging from 4 to 10.5, and preferably from 5 to 10. Among the basifying agents which may be used, there may be mentioned alkanolamines, alkali metal hydroxides or carbonates, ammonium hydroxide or ammonium carbonate. Among the acidifying agents which may be used, there may be mentioned lactic acid, acetic acid, tartaric acid, phosphoric acid, hydrochloric acid and citric acid.

The dye composition according to the invention may additionally contain various common adjuvants, such as antioxidants, fragrances, sequestering agents, film-forming products and treatment agents, dispersing agents, hair-conditioning agents, preserving agents, opacifying agents and any other adjuvant which is usually used in cosmetics.

The dye composition according to the invention may be provided in the various forms commonly used for dyeing hair, such as liquids which are thickened or gelled, creams, aerosol foams or any other forms which are suitable for dyeing keratinous fibers.

The present invention also relates to a process for dyeing keratinous fibers, and in particular human hair, which consists in allowing the dye composition defined above to act on the dry or wet keratinous fibers. The composition according to the invention may be used as a non-rinsed lotion, that is to say that the composition according to the invention is applied to the keratinous fibers and is then dried without intermediate rinsing. In other modes of application, the dye composition according to the invention is applied to the keratinous fibers for an exposure time ranging between 3 and 60 minutes, preferably between 5 and 45 minutes, and the fibers are rinsed, optionally washed and rinsed again, and then dried.

In order to gain a better understanding of the subject of the invention, several modes of implementation thereof will now be described, purely as guides and with no limitation being implied.

PREPARATION EXAMPLES

Example 1

Preparation of 1-(γ-hydroxypropyl) amino-4-(N-methyl-N-β-hydroxyethyl)amino-2-nitrobenzene hydrochloride named according to the IUPAC nomenclature 3-{4-[(2-hydroxyethyl) methylamino]-2-nitrophenylamino}-1-propanol hydrochloride The suspension of 51.0 g (0.2 mol) of 1-(γ-hydroxypropylamino)-4-(β-hydroxyethyl)amino-2- nitrobenzene and 30 g of calcium carbonate in 80 ml of water is heated in a hot water bath (50° C.). 18.7 ml (0.3 mol) of methyl iodide are added dropwise over 1 hour and the heating is continued for 7 hours, the reaction being monitored by thin layer chromatography (silica gel; eluent: ethyl acetate).

The mixture is filtered while hot and the filtrate is cooled: the oil which precipitates is extracted with ethyl acetate.

The ethyl acetate phase is dried over sodium sulfate, filtered and evaporated to dryness under reduced pressure.

The oil obtained is purified by passage through a medium pressure column (silica gel; gradient of ethyl acetate and heptane).

After evaporation of the solvent to dryness, the free base is dissolved in 150 ml of absolute ethanol and 25 ml of approximately 7N hydrochloric acid solution in absolute ethanol are added.

The hydrochloride of the expected compound precipitates as yellow crystals, which are filtered off, washed with ethyl ether and dried over potassium hydroxide under vacuum.

22.1 g of hydrochloride are obtained, which product melts with decomposition at 189°–192° C. and the elemental analysis of which, calculated for $C_{12}H_{20}N_3O_4Cl$, is:

|  | C % | H % | N % | O % | Cl % |
| --- | --- | --- | --- | --- | --- |
| Calculated: | 47.14 | 6.59 | 13.74 | 20.93 | 11.59 |
| Found: | 47.24 | 6.71 | 13.59 | 21.20 | 11.66 |

Example 2

Preparation of 1-(γ-hydroxypropyl)amino-4-(N-ethyl-N-β-hydroxyethyl)amino-2-nitrobenzene hydrochloride, named according to the IUPAC nomenclature 3-{4-[ethyl(2-hydroxyethyl)amino]-2-nitrophenylamino}-1-propanol hydrochloride This compound is prepared and purified according to the procedure described for the above example.

Starting with 51.0 g (0.2 mol) of 1-(γ-hydroxypropyl)amino-4-(β-hydroxyethyl)amino-2-nitrobenzene and 1-iodoethane, yellow crystals of hydrochloride (33.1 g) are obtained, which product melts with decomposition at 168°–170° C. and the elemental analysis of which, calculated for $C_{13}H_{22}N_3O_4Cl$, is:

|  | C % | H % | N % | O % | Cl % |
| --- | --- | --- | --- | --- | --- |
| Calculated: | 48.83 | 6.93 | 13.14 | 20.01 | 11.09 |
| Found: | 49.05 | 6.99 | 12.92 | 20.10 | 10.94 |

Example 3

Preparation of 1-(γ-hydroxypropyl)amino-4-(N-n-propyl-N -β-hydroxyethyl)amino-2-nitrobenzene hydrochloride, named according to the IUPAC nomenclature 3-{4-[(2-hydroxyethyl)propylamino]-2-nitrophenylamino}-1-propanol hydrochloride This compound is prepared and purified according to the procedure described for Example 1.

Starting with 51.0 g (0.2 mol) of 1-(γ-hydroxypropyl) amino-4-(β-hydroxyethyl)amino-2-nitrobenzene and 1-bromopropane, yellow crystals of hydrochloride (43.7 g) are obtained, which product melts with decomposition at 140°–142° C. and the elemental analysis of which, calculated for $C_{14}H_{24}N_3O_4Cl$, is:

|  | C % | H % | N % | O % | Cl % |
| --- | --- | --- | --- | --- | --- |
| Calculated: | 50.37 | 7.25 | 12.59 | 19.17 | 10.62 |
| Found: | 50.28 | 7.32 | 12.62 | 19.41 | 10.45 |

Example 4

Preparation of 1-(γ-hydroxypropyl)amino-4-(N-β-hydroxyethyl-N-γ-hydroxypropyl)amino-2-nitrobenzene hydrochloride, named according to the IUPAC nomenclature 3-{4-[(2-hydroxyethyl)(3-hydroxypropyl)amino]-2-nitro-phenylamino}-1-propanol hydrochloride This compound is prepared and purified according to the procedure described for Example 1.

Starting with 33.2 g (0.13 mol) of 1-(γ-hydroxypropyl) amino-4-(β-hydroxyethyl)amino-2-nitrobenzene and 3-chloro-1-propanol, yellow crystals of hydrochloride (16.3 g) are obtained, which product melts with decomposition at 100°–102° C. and the elemental analysis of which, calculated for $C_{14}H_{24}N_3O_4Cl+½H_2O$ [sic], is:

|  | C % | H % | N % | O % | Cl % |
| --- | --- | --- | --- | --- | --- |
| Calculated: | 46.86 | 7.02 | 11.71 | 24.52 | 9.88 |
| Found: | 46.93 | 6.99 | 11.74 | 23.96 | 10.11 |

Example 5

Preparation of 1-(γ-hydroxypropyl)amino-4-N,N-bis (γ-hydroxypropyl) amino-2-nitrobenzene hydrochloride, named according to the IUPAC nomenclature 3-{4-[bis(3-hydroxypropyl)amino]-2-nitrophenylamino}-1-propanol hydrochloride 1) 1st Stage:

Preparation of 4-fluoro-3-nitro-1-N,N-bis(γ-hydroxypropyl)aminobenzene

The suspension of 156.1 g (1 mol) of 4-fluoro-3-nitroaniline, 236.3 g of 3-chloro-1-propanol and 200 g of calcium carbonate in 500 ml of water is heated for 20 hours in a boiling water bath.

The reaction mixture is filtered while hot and the filtrate is cooled and extracted with ethyl acetate.

The ethyl acetate phase is dried over sodium sulfate, filtered and evaporated to dryness under reduced pressure.

The crystalline compound obtained is purified by passage through a medium pressure column (silica gel; gradient of ethyl acetate and heptane).

After evaporation of the solvent to dryness and recrystallization from boiling isopropyl acetate, 84 g of 4-fluoro-3-nitro-1-N,N-bis(γ-hydroxypropyl)aminobenzene are obtained, the melting point of which is 69° C. and the elemental analysis of which, calculated for $C_{12}H_{17}N_2O_4F$, is:

|  | C % | H % | N % | F % |
| --- | --- | --- | --- | --- |
| Calculated | 52.94 | 6.29 | 10.29 | 6.98 |
| Found | 53.02 | 6.46 | 10.29 | 7.01 |

2) 2nd Stage

Preparation of 1-(γ-hydroxypropyl)amino-4-N,N-bis (γ-hydroxypropyl)amino-2-nitrobenzene hydrochloride A solution of 54.4 g (0.2 mol) of the 4-fluoro-3-nitro-1-N,N-bis(γ-hydroxypropyl)aminobenzene obtained in the first stage and 30 g of 3-amino-1-propanol in 50 ml of dioxane is heated for 4 hours in a boiling water bath.

The reaction medium is poured into 400 ml of ice-cold water, neutralized with a 36% hydrochloric acid solution and extracted with ethyl acetate.

The ethyl acetate phase is dried over magnesium sulfate, filtered and evaporated to dryness under reduced pressure.

The oil obtained is purified by passage through a medium pressure column (silica gel; gradient of ethyl acetate and heptane).

After evaporation of the solvent to dryness, the free base is dissolved in 250 ml of absolute ethanol and 15 ml of approximately 7N hydrochloric acid solution in absolute ethanol are added.

The hydrochloride of the expected compound precipitates as yellow crystals, which are filtered off, washed with ethyl ether and dried over potassium hydroxide under vacuum.

16 g of hydrochloride are obtained, which product melts with decomposition at 155°–157° C. and the elemental analysis of which, calculated for $C_{15}H_{26}N_3O_5Cl$, is:

|  | C % | H % | N % | O % | Cl % |
| --- | --- | --- | --- | --- | --- |
| Calculated: | 49.52 | 7.20 | 11.55 | 21.99 | 9.74 |
| Found: | 49.51 | 7.25 | 11.43 | 22.14 | 9.84 |

Example 6

Preparation of 1-(β-hydroxyethyl )amino-4-N,N-bis (γ-hydroxypropyl) amino-2-nitrobenzene hydrochloride, named according to the IUPAC nomenclature 3-||4-(2-hydroxyethylamino)-3-nitrophenyl|(3-hydroxypropyl)amino|-1-propanol hydrochloride This compound is prepared and purified according to the procedure described for Example 5 (Stage 1).

Starting with 54.4 g of 4-fluoro-3-nitro-1-N,N -bis(γ-hydroxypropyl)aminobenzene, obtained in the first stage of Example 5, and 29.2 g of ethanolamine, yellow crystals of hydrochloride (22.4 g) are obtained, which product melts with decomposition at 170°–172° C. and the elemental analysis of which, calculated for $C_{14}H_{24}N_3O_5Cl$, is:

|  | C % | H % | N % | O % | Cl % |
| --- | --- | --- | --- | --- | --- |
| Calculated: | 48.07 | 6.92 | 12.01 | 22.87 | 10.13 |
| Found: | 48.06 | 7.01 | 11.92 | 22.83 | 10.04 |

Example 7

Preparation of 1-(γ-hydroxypropyl)amino-4-(N-ethyl-N-γ-hydroxypropyl)amino-2-nitrobenzene hydrochloride, named according to the IUPAC nomenclature 3-{4-|ethyl(3-hydroxypropyl)amino|-2-nitrophenylamino}-1-propanol hydrochloride 1) 1st Stage:

Preparation of 1-(γ-hydroxypropyl)amino-3-nitro-4-(γ-hydroxypropyl)aminobenzene

A solution of 15.0 g (0.07 mol) of 4-fluoro-3-nitro-1-(γ-hydroxypropyl)aminobenzene in 30 ml of 3-amino-1-propanol and 5 ml of dioxane is heated for 3 hours in a boiling water bath.

The reaction mixture is poured into 250 ml of ice-cold water, neutralized with a 36% hydrochloric acid solution and extracted with ethyl acetate.

The ethyl acetate phase is dried over sodium sulfate, filtered and evaporated to dryness under reduced pressure.

The oil obtained is purified by passage through a medium pressure column (silica gel; gradient of ethyl acetate and heptane).

After evaporation of the solvent to dryness, 10 g of a violet oil of 1-(γ-hydroxypropyl)amino-3-nitro-4-(γ-hydroxypropyl)aminobenzene are obtained, the elemental analysis of which, calculated for $C_{12}H_{19}N_3O_4$, is:

|  | C % | H % | N % | O% |
| --- | --- | --- | --- | --- |
| Calculated | 53.52 | 7.11 | 15.60 | 23.76 |
| Found | 53.96 | 7.23 | 15.46 | 24.07 |

2) 2nd Stage:

Preparation of 1-(γ-hydroxypropyl)amino-4-(N-ethyl-N-γ-hydroxypropyl)amino-2-nitrobenzene hydrochloride This compound is prepared and purified according to the procedure described for Example 1.

Starting with 9.3 g (0.034 mol) of 1-(γ-hydroxypropyl) amino-3-nitro-4-(γ-hydroxypropyl)aminobenzene prepared above (Stage 1) and ethyl iodide, yellow crystals of 1-(γ-hydroxypropyl)amino-4-(N-ethyl-N-γ-hydroxypropyl) amino-2-nitrobenzene hydrochloride (5.0 g) are obtained, which product melts with decomposition at 130°–132° C. and the elemental analysis of which, calculated for $C_{14}H_{24}N_3O_4Cl$, is:

|  | C % | H % | N % | O % | Cl % |
| --- | --- | --- | --- | --- | --- |
| Calculated | 50.37 | 7.25 | 12.59 | 19.17 | 10.62 |
| Found | 50.39 | 7.18 | 12.72 | 19.50 | 10.64 |

Example 8

Preparation of 1-(β-hydroxyethyl)amino-4-(N-ethyl-N-γ-hydroxypropyl)amino-2-nitrobenzene hydrochloride, named according to the IUPAC nomenclature 3-{ethyl|4-(2-hydroxyethylamino)-3-nitrophenyl|amino}-1-propanol hydrochloride 1) 1st Stage:

Preparation of 1-(γ-hydroxpropyl)amino-3-nitro-4-(β-hydroxyethyl)aminobenzene

The procedure described for Example 7 (1st Stage) is followed.

Starting with 15.0 g (0.07 mol) of 4-fluoro-3-nitro-1-(γ-hydroxypropyl)aminobenzene in 30 ml of ethanolamine and 5 ml of dioxane, 11 g of a violet oil of 1-(γ-hydroxypropyl)amino-3-nitro-4-(β-hydroxyethyl) aminobenzene are obtained, the elemental analysis of which, calculated for $C_{11}H_{17}N_3O_4$, is:

|  | C % | H % | N % | O % |
|---|---|---|---|---|
| Calculated | 51.76 | 6.71 | 16.46 | 25.07 |
| Found | 52.28 | 7.15 | 16.45 | 25.47 |

2) 2nd Stage:

Preparation of 1-(β-hydroxyethyl)amino-4-(N-ethyl-N-γ-hydroxypropyl)amino-2-nitrobenzene hydrochloride This compound is prepared and purified according to the procedure described for Example 1.

Starting with 11.0 g (0.047 mol) of 1-γ-hydroxypropylamino-3-nitro-4-(β-hydroxyethyl) aminobenzene prepared above (Stage 1) and ethyl iodide, yellow crystals of 1-(β-hydroxyethyl)amino-4-(N-ethyl-N-γ-hydroxypropyl)amino-2-nitrobenzene hydrochloride (6.9 g) are obtained, which products melts with decomposition at 168°–170° C. and the elemental analysis of which, calculated for $C_{13}H_{22}N_3O_4Cl$, is:

|  | C % | H % | N % | O % | Cl % |
|---|---|---|---|---|---|
| Calculated | 48.83 | 6.93 | 13.14 | 20.01 | 11.09 |
| Found | 48.94 | 7.06 | 12.94 | 20.18 | 10.84 |

Example 9

Preparation of 1-(β-hydroxypropyl)amino-4-(N-methyl-N-γ-hydroxypropyl)amino-2-nitrobenzene hydrochloride, named according to the IUPAC nomenclature 3-{[4-(2-hydroxypropylamino)-3-nitrophenyl]methylamino}-1propanolhydrochloride 1) 1st Stage:

Preparation of 1-(γ-hydroxypropyl)amino-3-nitro-4-(β-hydroxypropyl)aminobenzene

A solution of 15.0 g (0.07 mol) of 4-fluoro-3-nitro-1-(γ-hydroxypropyl)aminobenzene in 30 ml of 1-amino-2-propanol and 5 ml of dioxane is heated for 2 hours in a boiling water bath.

The reaction medium is poured into 250 ml of ice-cold water and neutralized with a 36% hydrochloric acid solution.

The red crystalline precipitate is filtered off, washed with water, recrystallized from boiling 96° alcohol and dried under vacuum.

17 g of 1-(γ-hydroxypropyl)amino-3-nitro-4-(β-hydroxypropyl)aminobenzene are obtained, the melting point of which is 119° C. and the elemental analysis of which, calculated for $C_{12}H_{19}N_3O_4$, is:

|  | C % | H % | N % | O % |
|---|---|---|---|---|
| Calculated: | 53.52 | 7.11 | 15.60 | 23.76 |
| Found: | 53.63 | 7.13 | 15.61 | 24.02 |

2) 2nd Stage:

Preparation of 1-(β-hydroxypropyl) amino-4-(N-methyl-N-γ-hydroxypropyl)amino-2-nitrobenzene hydrochloride This compound is prepared and purified according to the procedure described for Example 1.

Starting with 16.5 g (0.061 mol) of 1-(γ-hydroxypropyl)amino-3-nitro-4-(β-hydroxypropyl)aminobenzene prepared above (Stage 1) and methyl iodide, yellow crystals of 1-(β-hydroxypropyl)amino-4-(N-methyl-N-γ-hydroxypropyl)amino-2-nitrobenzene (5.9 g) are obtained, which product melts with decomposition at 158°–160° C. and the elemental analysis of which, calculated for $C_{13}H_{22}N_3O_4Cl+\frac{1}{4}H_2O$, is:

|  | C % | H % | N % | O % | Cl % |
|---|---|---|---|---|---|
| Calculated | 48.15 | 6.99 | 12.96 | 20.97 | 10.93 |
| Found | 48.23 | 6.94 | 13.04 | 20.89 | 10.92 |

DYEING EXAMPLES

Example A

The following dye composition is prepared:

| | |
|---|---|
| 1-(γ-Hydroxypropyl)amino-4-(N-methyl-N-β-hydroxyethyl)amino-2-nitrobenzene hydrochloride | 0.92 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above composition is applied to natural grey hair containing 90% white hairs. It is left to stand for 30 minutes at room temperature. After rinsing and drying, the hair is dyed in an ash-dark purple color.

Example B

| | |
|---|---|
| 1-(γ-Hydroxypropyl)amino-4-(N-ethyl-N-β-hydroxyethyl)amino-2-nitrobenzene hydrochloride | 0.96 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above composition is applied to natural grey hair containing 90% white hairs. It is left to stand for 30 minutes at room temperature. After rinsing and drying, the hair is dyed in an ash color.

Example C

The following dye composition is prepared:

| | |
|---|---|
| 1-(γ-Hydroxypropyl)amino-4-(N-β-hydroxyethyl-N-γ-hydroxypropyl)amino-2-nitrobenzene hydrochloride | 1.07 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above dye composition is applied to natural grey hair containing 90% white hairs. After standing for 30 minutes at room temperature, rinsing and drying, the hair is dyed in a slightly dark purple-ash color.

Example D

The following dye composition is prepared:

| | |
|---|---|
| 1-(γ-Hydroxypropyl)amino-4-N,N-bis(γ-hydroxypropyl)amino-2-nitrobenzene hydrochloride | 1.09 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above dye composition is applied to natural grey hair containing 90% white hairs. After standing for 30 minutes at room temperature, rinsing and drying, the hair is dyed in an ash color.

Example E

The following dye composition is prepared:

| | |
|---|---|
| 1-(β-Hydroxyethyl)amino-4-N,N-bis(γ-hydroxypropyl)amino-2-nitrobenzene hydrochloride | 1.05 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above dye composition is applied to natural grey hair containing 90% white hairs. After standing for 30 minutes at room temperature, rinsing and drying, the hair is dyed in an ash color.

Example F

The following dye composition is prepared:

| | |
|---|---|
| 1-(γ-Hydroxypropyl)amino-4-(N-ethyl-N-γ-hydroxypropyl)amino-2-nitrobenzene hydrochloride | 1 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above dye composition is applied to grey hair containing 90% white hairs which has been subjected to a permanent-wave treatment. After standing for 30 minutes at room temperature, rinsing and drying, the hair is dyed in an ash color.

Example G

The following dye composition is prepared:

| | |
|---|---|
| 1-(β-Hydroxyethyl)amino-4-(N-ethyl-N-γ-hydroxypropyl)amino-2-nitrobenzene hydrochloride | 0.96 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol q.s. pH 9 | |
| Water q.s. for | 100 g |

The above dye composition is applied to permanent-waved grey hair containing 90% white hairs. After standing for 30 minutes at room temperature, rinsing and drying, the hair is dyed in a slightly ash-dark purple color.

Example H

The following dye composition is prepared:

| | |
|---|---|
| 1-(γ-Hydroxypropyl)amino-4-(N-ethyl-N-β-hydroxyethyl)amino-2-nitrobenzene hydrochloride | 0.5 g |
| 1-β-Hydroxyethyloxy-3-methylamino-2-nitrobenzene | 0.07 g |
| Oxyethylenated nonylphenol containing 9 mol of ethylene oxide | 8 g |
| Coconut fatty acid diethanolamides | 2 g |
| Ethyl glycol | 10 g |
| Triethanolamine q.s. pH 9 | |
| Water q.s. for | 100 g |

This composition is applied to permanent-waved grey hair containing 90% white hairs. After standing for 20 minutes at room temperature, rinsing and drying, the hair is dyed in ash-light blond.

We claim:

1. Hydroxypropylated 2-nitro-p-phenylenediamine having the formula:

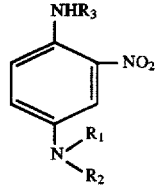
(I)

in which:

$R_1$ represents a $C_1$–$C_4$ alkyl radical, $R_2$ and $R_3$, independently of one another, represent a β-hydroxyethyl, β-hydroxypropyl, γ-hydroxypropyl or β,γ-dihydroxypropyl radical, with the proviso that at least one of the radicals $R_2$ or $R_3$ represents a γ-hydroxypropyl radical and cosmetically acceptable salts thereof.

2. Compound according to claim 1, wherein the $C_1-C_4$ alkyl group represented by $R_1$ is a methyl, ethyl or n-propyl radical.

3. Compound according to claim 1, wherein the compound is 1-(γ-hydroxypropyl)amino-4-(N-ethyl-N-β-hydroxyethyl) -amino-2-nitrobenzene, 1-(γ-hydroxypropyl) amino-4-(N -methyl-N-β-hydroxyethyl)amino-2-nitrobenzene, 1-(γ-hydroxypropyl)amino-4-(N-n-propyl-N-β-hydroxyethyl)amino -2-nitrobenzene, 1-(γ-hydroxypropyl) -amino-4-(N-ethyl-N-γ-hydroxypropyl) amino-2-nitrobenzene, 1-(β-hydroxyethylamino-4-(N-ethyl-N-γ-hydroxypropyl) -amino-2-nitrobenzene, 1-(β-hydroxypropyl)amino -4-(N-methyl-N-γ-hydroxypropyl) amino-2-nitrobenzene or the cosmetically acceptable salts thereof.

4. Dye composition for the direct dyeing of keratinous fibers, wherein the composition contains, in an aqueous, alcoholic or aqueous-alcoholic vehicle, 0.01 to 10% by weight, expressed as free base, of at least one compound of the formula (I)

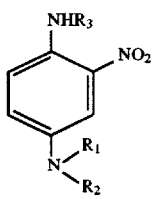

in which:

$R_1$ represents a $C_1-C_4$ alkyl radical, $R_2$ and $R_3$, independently of one another, represent a β-hydroxyethyl, β-hydroxypropyl, γ-hydroxypropyl or β,γ-dihydroxpropyl radical, with the proviso that at least one of the radicals $R_2$ or $R_3$ represents a γ-hydroxpropyl radical, or of the formula (II')

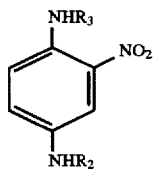

in which the radical $R_2$ is the γ-hydroxypropyl radical and the radical $R_3$ is a β-hydroxvethyl, β-hydroxvpropyl or γ-hydroxypropyl radical, or one of the cosmetically acceptable salts thereof.

5. Dye composition according to claim 4, wherein the composition contains a compound of formula (I) which is 1-(γ-hydroxypropyl) amino-4-(N-ethyl-N-β-hydroxyethyl) amino-2-nitrobenzene, 1-(γ-hydroxypropyl)amino-4-(N-methyl-Nβ-hydroxyethyl) -amino-2-nitrobenzene, 1-(γ-hydroxypropyl)amino-4-(N-n -propyl-N-β-hydroxyethyl) amino-2-nitrobenzene,|1-(γ-hydroxypropyl) amino-4-N,N-bis (γ-hydroxypropyl) amino -2-nitrobenzene,1-(β-hydroxyethyl) amino-4,N,N-bis(γ-hydroxypropyl)amino -2nitrobenzene [|sic]], 1(γ-hydroxypropyl)amino -4-(N-β-hydroxyethyl-N-γ-hydroxypropyl)amino-2-nitrobenzene ] 1(γ-hydroxypropyl)amino-4-hydroxypropyl)amino-2-nitrobenzene, 1-(β-hydroxyethyl)amino-4-(N-ethyl-N -γ-hydroxypropyl)amino-2-nitrobenzene,|[sic]| and 1-(β-hydroxypropyl) amino-4-(N-methyl-N-γ-hydroxypropyl) amino-2-nitrobenzene or the cosmetically acceptable salts thereof.

6. Dye composition for the direct dyeing of keratinous fibers, wherein the composition contains in an aqueous, alcoholic or aqueous-alcoholic vehicle, 0.01 to 10% by weight, expressed as free base of at least one compound of the formula (I)

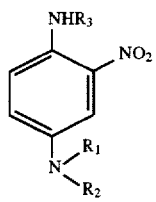

in which:

$R_1$ represents a $C_1-C_4$ alkyl, β-hydroxyethyl, β-hydroxypropyl or γ-hydroxypropyl radical, $R_2$ and $R_3$, independently of one another, represent a β-hydroxyethyl, β-hydroxypropyl, γ-hydroxypropyl or β,γ-dihydroxypropyl radical, with the proviso that at least one of the radicals $R_1$, $R_2$ or $R_3$ represents a γ-hydroxypropyl radical and that the other two radicals cannot simultaneously denote a β-hydroxyethyl radical, or of the formula (II')

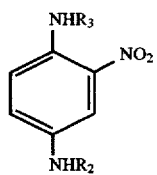

in which the radical $R_2$ is the γ-hydroxypropyl radical and the radical $R_3$ is a β-hydroxyethyl, β-hydroxypropyl or γ-hydroxypropyl radical, or one of the cosmetically acceptable salts thereof, in combination with at least one yellow or green-yellow nitrobenzene dye which is 1-β-hydroxyethyloxy-3-methylamino-4-nitrobenzene, 1-(methylamino)-2-nitro-5-(β,γ-dihydroxypropyl) oxybenzene, 1-(β-hydroxyethylamino)-2-methoxy-4-nitrobenzene, 1-(β-aminoethylamino)-2-nitro-5-methoxybenzene, 1,3-di(β-hydroxyethylamino)-4-nitro-6-chlorobenzene, 1-amino-2-nitro-6-methylbenzene, 1-(β-hydroxyethyl-amino)-2-hydroxy -4- nitrobenzene, N-(β-hydroxyethyl)-2-nitro-4-trifluoromethyl- aniline, 4-β-hydroxy-ethylamino-3-nitrobenzene-sulfonic acid, 4-ethylamino-3-nitrobenzoic acid, 4-(β-hydroxy-ethyl) amino-3-nitrochlorobenzene, 4-(β-hydroxyethyl)amino-3-nitromethylbenzene, 4-(β,γ-dihydroxypropyl)amino-3-nitrotrifluoro-methylbenzene, 1-β-ureidoethylamino-4-nitrobenzene, 0,N-bis(β-hydroxyethyl)-2-amino-5-nitrophenol, 1-hydroxy-2-amino-5-nitrobenzene, 1-amino-2-[tris(hydroxymethyl)-methyl]amino-5-nitrobenzene, 1-(β-hydroxyethyl)amino-2-nitrobenzene or 4-(β-hydroxyethylamino)-3-nitrobenzamide.

7. Dye composition according to claim 4 or 6 wherein the composition contains red nitrobenzene dyes which are 1-hydroxy-3-nitro-4-(γ-hydroxypropylamino)benzene, N-(β-hydroxyethyl)amino-3-nitro-4-aminobenzene,[[sic]], 1-amino-3-methyl-4-(β-hydroxyethyl)amino-6-nitrobenzene, 1-hydroxy-3-nitro-4-N-(β-hydroxyethyl) aminobenzene,1,4-diamino-2-1nitrobenzene, -amino-2-nitro-4-methylaminobenzene, N-(β-hydroxyethyl)-2-nitro-para-phenylenediamine, 1-amino-2-nitro -4-(β-hydroxyethylamino)-5-chlorobenzene, 2-nitro-4-aminodiphenylamine or 1-amino-3-nitro-6-hydroxybenzene.

8. Dye composition according to claim 4 or 6, wherein the composition contains orange nitrobenzene dyes which are 1-(β-aminoethyl)amino-2-nitro-4-(β-hydroxyethyl)oxybenzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethylamino)benzene 2-nitro-4'-hydroxydiphenylamine or 1-amino-2-nitro-4-hydroxy-5-methylbenzene.

9. Dye composition according to claim or 4 or 6, wherein the composition contains direct dyes which are azo dyes, anthraquinone dyes, triarylmethane derivatives or basic dyes.

10. Dye composition according to claim 6, wherein the composition contains 0.05 to 3% by weight of yellow or green-yellow nitrobenzene dyes.

11. Dye composition according to claim 4 or 6, wherein the composition additionally contains 0.05 to 10% by weight of direct dyes other than those of formula (I) or (II') and other than yellow or green-yellow nitrobenzene dyes.

12. Dye composition according to claim 4 or 6, wherein the composition contains organic solvents which are alcohols, glycols or glycol ethers, in concentrations of between 0.5 and 20% by weight, relative to the total weight of the composition.

13. Dye composition according to claim 4 or 6, wherein the composition contains at least one adjuvant selected from the group consisting of fatty amides in concentrations of between 0.05 and 10% by weight, anionic, cationic, nonionic or amphoteric surface-active agents, or mixtures thereof, in concentrations of between 0.1 and 50% by weight, thickening agents in concentrations of between 0.2 and 5% by weight, antioxidants, fragrances, sequestering agents, film-forming agents, hair-treatment agents, dispersing agents, hair-conditioning agents, preserving agents and opacifying agents.

14. Dye composition according to claim 4 or 6, wherein the composition has a pH of between 4 and 10.5.

15. Process for dyeing keratinous fibers by direct dyeing, wherein an effective amount for dyeing said fibers of the dye composition according to claim 4 or 6 is applied to the keratinous fibers, and these keratinous fibers are dried without intermediate rinsing.

16. Process for dyeing keratinous fibers by direct dyeing, wherein an effective amount for dyeing said fibers of the dye composition according to claim 4 or 6 is applied to the keratinous fibers, and after leaving the composition to act for 3 to 60 minutes, the keratinous fibers are rinsed and then dried.

17. Dye composition according to claim 4 or 6, wherein the composition contains 0.1 to 5% by weight, expressed as free base, of a compound of formula (I) or (II').

* * * * *